PLT-239 SR
C5203 OR PP 001,881
BEST AVAILABLE COPY
Nov. 24, 1959 H. KERRIGAN Plant Pat. 1,881
AZALEA PLANT
Filed April 1, 1959
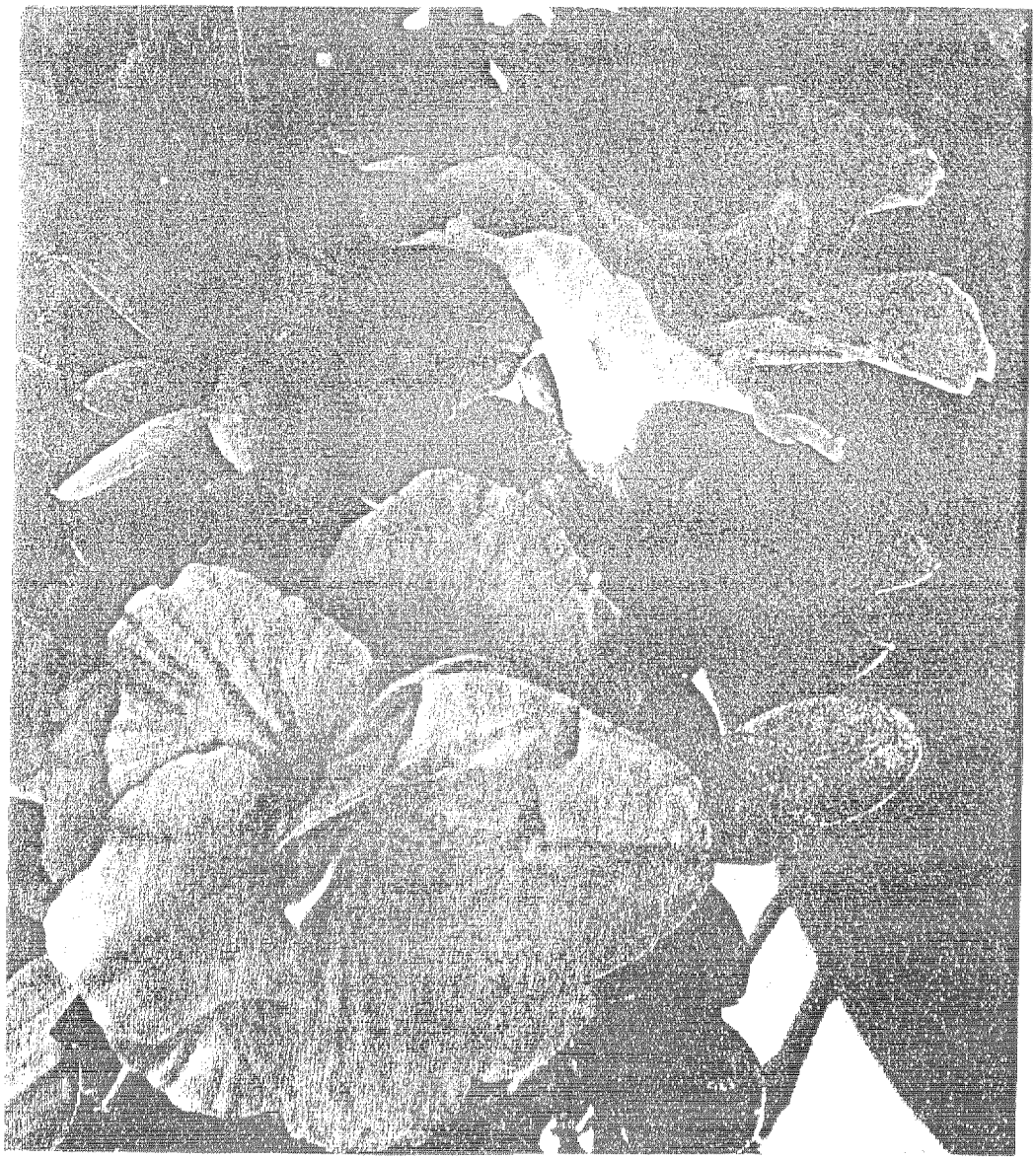

United States Patent Office

Plant Pat. 1,881
Patented Nov. 24, 1959

1,881

AZALEA PLANT

Howard Kerrigan, Oakland, Calif.

Application April 1, 1959, Serial No. 803,548

1 Claim. (Cl. 47—60)

This invention relates to a new and improved azalea plant, the principal new and different characteristics of which are the distinctive Carmine Rose flower, exceptional form, vigorous growth habit and prolific blooming quality. The azalea plant was derived as a hybrid from Paul Schame (unpatented) and Madame Pericat (unpatented), both of which azalea plants are well known to the trade. The azalea plant is distinguished by the characteristics mentioned. The new variety of azalea plant has been asexually reproduced at Oakland, California, by cuttings which retain the characteristics of the parent.

In the accompanying drawing the figure shows a typical flower, the drawing representing approximate actual size.

A detailed description of this new variety of azalea plant follows:

*Habit of growth.*—Vigorous, bushy and compact in growth, responding well to pruning which encourages and produces numerous branches.

*Foliage.*—Medium in size, dark green in color. The leaves and branches are lightly veined and covered with fine, hair-like fibers. The immature branches are greenish brown becoming brown at maturity. The mature leaf is approximately two inches (2") in length and three quarters (¾") of an inch in width.

*Flowers.*—The flowers are a combination of the hose-in-hose and the double Belgian Indica type, having the double corolla of the hose-in-hose type combined with the characteristic petaloids of the Belgian. The double flower has overlapping petals forming two distinct corollas, while the corolla is split in such fashion as to suggest many distinct petals. These petals and petaloids are fifteen in number on the average.

The normal blooming season (in the Oakland, California, temperature climate) begins about early March. When the flower first opens the petals are Carmine Rose (British Horticultural Chart #621, fading to #621/1 and #621/2). In maturity the overall color fades to #621/1 and #621/2. The inside of the mature flower is splotched with the darkest shade of Carmine Rose (British Horticultural Chart #621). The base of the flower is flesh color.

*Ovary.*—Pale green in color with white hair-like fibers. Normal size.

*Sepals.*—None.

*Stem.*—Five eighths inch (⅝") in length on the average covered with white hair-like fibers. Color is pale green.

*Stamens.*—Slender, one inch (1") in length on the average. Color is either flesh or mustard.

*Pistil.*—The style is one and one eighth (1⅛") inches in length on the average, flesh in color with pale yellow stigma.

*Buds.*—Pale green in color with hair-like fibers on the outer surface. The mature bud is five eighths inches (⅝") in length on the average and one quarter of an inch (¼") in width (at the widest point) on the average.

*Parentage.*—Paul Schame (unpatented) and Madame Pericat (unpatented).

It is recognized that the plant will vary somewhat with the season and growing conditions, although it will nevertheless retain its distinctive characteristics and properties.

Color designations as given above that are not identified by reference to the British Horticultural Color Chart are used according to their ordinary dictionary meaning.

Having thus disclosed my discovery I claim:

The new and distinct variety of azalea plant herein described and illustrated, characterized by the distinctive Carmine Rose flower, exceptional form, prolific blooming habit, and dense, vigorous, compact growth.

No references cited.